United States Patent
Yan et al.

(10) Patent No.: US 6,324,240 B1
(45) Date of Patent: Nov. 27, 2001

(54) METHOD FOR BEAM HARDENING CORRECTION IN QUANTITATIVE COMPUTED X-RAY TOMOGRAPHY

(75) Inventors: Chye Hwang Yan, Ang Mo Kio (SG); Robert T. Whalen, Los Altos; Sandy Napel, Menlo Park, both of CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/438,218

(22) Filed: Nov. 12, 1999

Related U.S. Application Data

(60) Provisional application No. 60/108,257, filed on Nov. 12, 1998.

(51) Int. Cl.$^7$ ................................................... A61B 6/03
(52) U.S. Cl. ........................... 378/4; 378/8; 378/901
(58) Field of Search ............................. 378/4, 8, 15, 901

(56) References Cited

U.S. PATENT DOCUMENTS 6,018,562 * 1/2000 Wilson .................................. 378/9

OTHER PUBLICATIONS

Joseph, P. et al., *a method for simultaneous correction of spectrum hardening artifacts in CT images containing both bone and iodine*, Med. Phys., 24(10), pp. 1629–1634, Oct. 1997.

Chase, R., et al., *An improved image algorithm for CT scanners*, Med. Phys., 5(6), pp. 497–499, Nov./Dec. 1978.

Alvarez, R. et al., *Energy–selective reconstructions in X–ray computerized tomography*, Phys. Med. Biol., 21(5), pp. 733–744, 1976.

Duerinckx, A. et al., *Polychromatic streak artifacts in computed tomography images*, J. Comp. Assis. Tomography, vol. 2, pp. 481–487, Sep. 1978.

Joseph, P. et al., *A method for correcting bone induces artifacts in computed tomography Scanners*, J. Comp. Assis. Tomography, vol. 2, pp. 100–108, Jan. 1978.

Kijewski, P. et al., *Correction for beam hardening in computed tomography*, Med. Phys., 5(3), pp. 209–214, May/Jun. 1978.

McDavid, W. et al., *Correction for spectral artifacts in cross–sectional reconstruction from X–rays*, Med. Phys. 4(1), pp. 54–57, Jan./Feb. 1977.

Nalcioglu, O. et al., *Post–reconstruction method for beam hardening in computerised Tomography*, Phys. Med. Biol., 24(2), pp. 330–340, 1979.

* cited by examiner

*Primary Examiner*—David V. Bruce
(74) *Attorney, Agent, or Firm*—Lumen Intellectual Property Services

(57) ABSTRACT

Each voxel is assumed to contain exactly two distinct materials, with the volume fraction of each material being iteratively calculated. According to the method, the spectrum of the X-ray beam must be known, and the attenuation spectra of the materials in the object must be known, and be monotonically decreasing with increasing X-ray photon energy. Then, a volume fraction is estimated for the voxel, and the spectrum is iteratively calculated.

8 Claims, 2 Drawing Sheets

Not allowed**

Not allowed**

Allowed**

METHOD FOR BEAM HARDENING CORRECTION IN QUANTITATIVE COMPUTED X-RAY TOMOGRAPHY

RELATED APPLICATIONS

The present application claims the benefit of priority from copending provisional patent application 60/108,257, filed on Nov. 12, 1998, which is hereby incorporated by reference.

This invention was made with U.S. Government support under grant numbers NCC-5186 and NCC2-5088 awarded by NASA. The National Institutes of Health also supported the development of the present invention under grant P41-RR09784. The Government has certain rights in the invention.

FIELD OF THE INVENTION

The present invention relates generally to computer assisted tomography and quantitative computed tomography (both known as CT imaging). More particularly, it relates to a method for processing CT imaging data that corrects for beam hardening errors.

BACKGROUND OF THE INVENTION

CT imaging is extensively used for medical imaging and the imaging of objects. In CT imaging, X-rays are projected through the object being imaged, and these X-rays are detected by arrays of detectors. The X-rays are projected through the object in many different directions. The combination of X-ray trajectories through the object provides data from which the internal structure of the object can be determined. Contrast in CT images is provided by variations in X-ray attenuation within the object. No other contrast parameters are available. Therefore, accurate measurements of X-ray attenuation are required for high quality CT images.

Quantitative computed tomography (QCT) is a technique that allows for quantitative measurements of physical properties related to X-ray attenuation. QCT has been used for in-vivo quantitative measurements of bone density, for example. The uses of QCT include assessment of spinal trabecular bone, evaluation of drug therapy in the treatment of osteoporosis, screening for osteoporosis, fracture risk assessment and many others. Although QCT is now an established tool for bone densitometry, there exist major issues affecting the accuracy and precision of QCT measurements.

QCT measurements and CT images are affected by beam hardening error in X-ray attenuation measurements. Beam hardening error is caused by the energy-dependence of X-ray transmission within an object being imaged. In any material, low-energy X-rays are attenuated more strongly than high-energy X-rays. Therefore, as a polychromatic X-ray beam passes through an object, the proportion of high energy X-rays in the beam increases, and attenuation decreases. Long path lengths through an object therefore appear to have an excessively small attenuation. When an image is computed, the center of an object appears to have a lower attenuation than the outer regions of the object. In this way, beam hardening error produces inaccurate measurements in QCT. Correction of beam hardening errors has been an active area of research since 1975. Some popular current correction techniques for beam hardening require strict assumptions about the X-ray attenuation characteristics of the materials within the object. The two most commonly used techniques are the water and bone corrections which assume that the materials in the scan field are either water-equivalent or dense bone-equivalent in X-ray attenuation characteristics. For more information regarding these techniques, reference can be made to "A Method for Correcting Bone Induced Artifacts in Computed Tomography Scanners" by P. M. Joseph and R. D. Spital in the *Journal of Computer Assisted Tomography* vol. 2, pp. 481–487, 1978 and "Post-Reconstruction Method for Beam Hardening in Computed Tomography" by O. Nalcioglu and R. Y. Lou in *Physics in Medicine and Biology*, vol 24, pp.330–340, 1979.

In another beam hardening correction method, calibration tubes having a known transmission characteristic are used. However, this method is often not effective for two reasons: 1) different regions in the scan field experience different degrees of beam hardening, and 2) calibration tubes cannot capture the beam hardening characteristics in vicinity of a patients bone because the calibration tube must be placed outside the body.

There exists a need in the art of CT imaging and QCT for an improved method of beam hardening correction. An improved beam hardening correction technique will provide QCT measurements and CT images with improved accuracy.

OBJECTS AND ADVANTAGES OF THE INVENTION

Accordingly, it is a primary object of the present invention to provide an improved method for beam hardening correction that:

1) accurately corrects beam hardening errors;
2) does not require knowledge of the attenuation characteristics of the X-ray detectors used in the CT imager;
3) does not require calibration tubes;
4) can be used with objects comprising many different materials.

These and other objects and advantages will be apparent upon reading the following description and accompanying drawings.

SUMMARY OF THE INVENTION

The present invention provides a method for beam hardening correction in CT imaging data. The present method includes reiterative calculations that converge on accurate measurements of X-ray attenuation. In a first variation of the present invention, the following information is required:

1) The attenuation spectra for materials within the object being imaged. Each voxel is assumed to contain at most two materials.
2) The output spectra of the X-ray source.
3) The output data from the X-ray detectors.

An initial estimation is made of volume fraction of the two materials in each voxel. Then, a reiterative calculation is performed that converges upon the true volume fraction for each material in each voxel.

In a second variation of the present invention, the following information is required:

1) Two basis attenuation spectra. The attenuation spectra do not need to correspond to real materials.
2) Output spectra from the X-ray source at two different settings (e.g. two different X-ray tube voltages).
3) Output data from the X-ray detectors at the two X-ray source settings.

An initial estimation is made of the relative weighting of the two basis attenuation spectra based on a linear combination of the basis spectra. Then, a reiterative calculation is performed that converges upon the relative weightings of the basis attenuation spectra that produce the observed measurements. A separate reiterative calculation is performed for each voxel. In this way, an accurate measurement of the attenuation spectrum for each voxel is provided.

DETAILED DESCRIPTION

Figure 1:
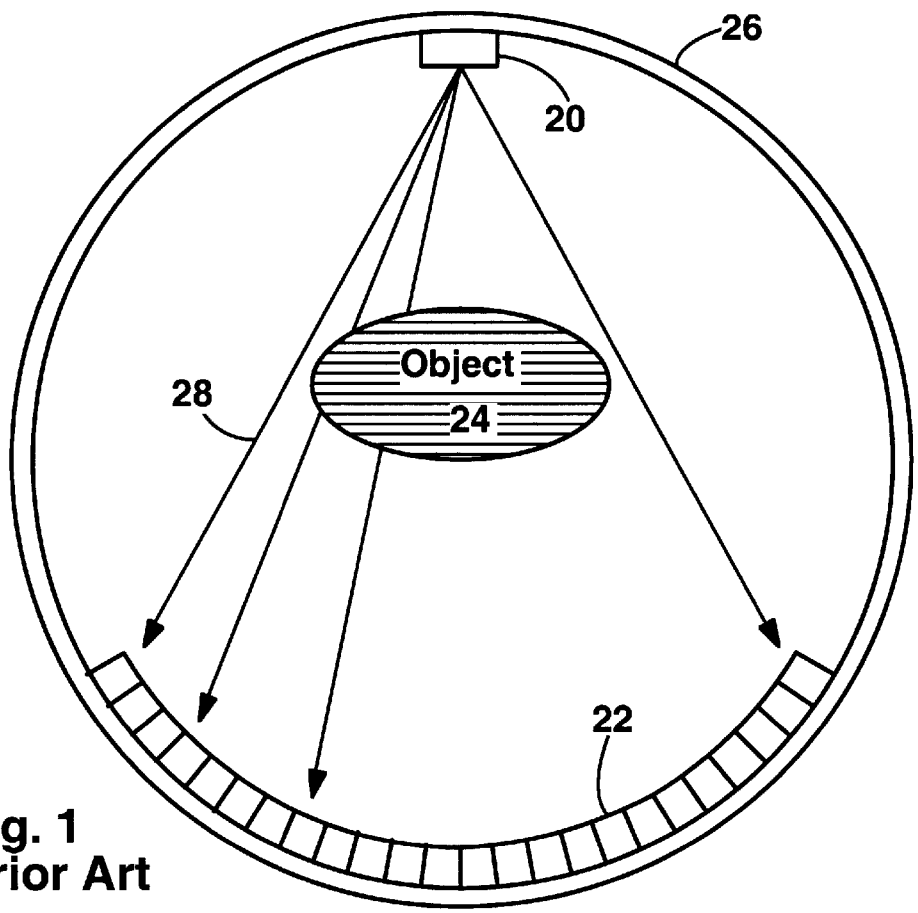
FIG. 1 (Prior Art) shows a CT imaging device as known in the art.

FIG. 1 shows a CT imaging device as known in the art of CT imaging. The device includes an X-ray source 20, such as an electron tube, and X-ray detectors 22. An object 24 to be imaged is disposed between the source 20 and detectors 22. The source and detectors are attached to a rigid frame 26 that is free to rotate around the object 24. X-ray beam paths 28 extend from the source to detectors through the object 24. In operation, X-ray intensity is measured at every detector at many different orientations of the rigid frame with respect to the object. The number of discrete measurement made in a complete scan is equal to N×K, where N is the number of positions of the frame used during a scan, and K is the number of detectors. In the following discussion, it is understood that there are N×K beam paths, with each beam path corresponding to an X-ray intensity measurement.

The object is divided into volume elements, or voxels. Each voxel within the object is located in the paths of several beam paths. Therefore, each voxel affects many X-ray intensity measurements. The challenge of CT imaging is to separate the X-ray attenuation contributions from each voxel.

THEORY

The attenuation along any beam path is a function of the attenuation coefficient of the material in the beam path and the energy spectrum of the X-ray source. For a given beam path r through the object, the corresponding detector measurement C is given by:

$$C(r) = -\log \int S(E) \exp(\int_r \mu(x,E)dx) dE$$

where:
1) S(E) is the energy spectrum of the X-ray source and must be known to the experimenter, and
2) $\mu(x,E)$ is the linear attenuation coefficient of a voxel at X-ray photon energy E and location x.

Consider the operator B defined by $B\mu = C$. The operator B is nonlinear with respect to $\mu$:

$$B(\mu_1+\mu_2) \neq B\mu_1 + B\mu_2$$

This nonlinear characteristic is the main cause of beam hardening artifacts in CT images.

The problem of calculating CT images while minimizing beam hardening errors can be restated as follows: given S(E) and C(r), find $\mu(x,E)$ that satisfies $C(r) = -\log \int S(E) \exp(\int_r \mu(x,E)dx)dE$.

The problem of constructing a CT image without beam hardening errors is to find $\mu(x,E)$ from the detector measurements C(r). Since $\mu(x,E)$ is a three-dimensional function, and C(r) is a two dimensional function, the problem is not well posed. In order to find a stable solution, $\mu(x,E)$ must be regularized. The present invention includes two different regularization methods associated with two different CT methods: single energy reconstruction and dual energy reconstruction.

Figure 2:
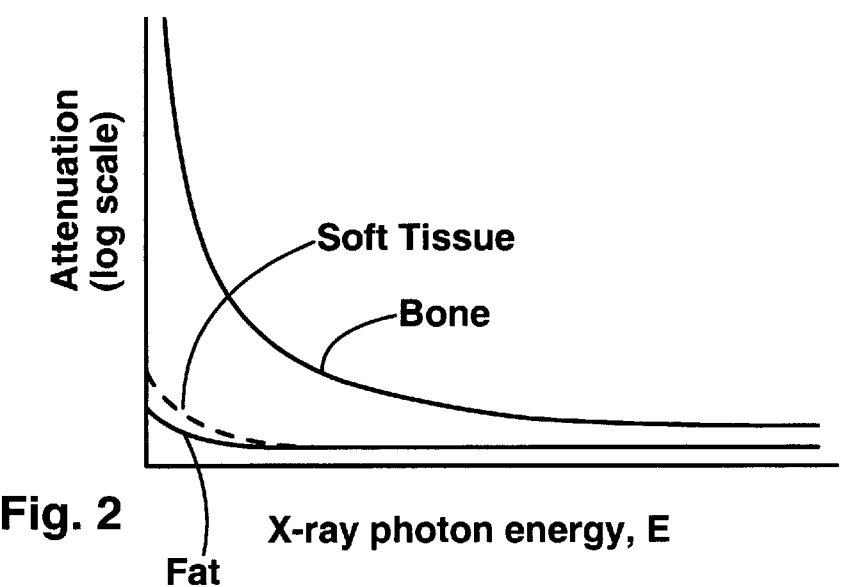
FIG. 2 shows exemplary attenuation spectra for bone, soft tissue and fat.

FIG. 2 shows typical relative attenuation coefficients $\mu(E)$ for bone, soft tissue and fat. The attenuation coefficients are monotonically decreasing with increasing E.

SINGLE ENERGY RECONSTRUCTION

In the single energy reconstruction embodiment of the present invention, it is necessarily assumed that each voxel consists of at most two different known materials. The materials may be different in each voxel. For a particular voxel at location x, the attenuation coefficient $\mu(x,E)$ can be written as a linear combination of two attenuation coefficients according to the equation $$\mu(x,E) = v(x)\mu_1(x,E) + (1-v(x))\mu_2(x,E)$$

where $\mu_1(x,E)$ is the attenuation coefficient for material 1, $\mu_2(x,E)$ is the attenuation coefficient for material 2, and v(x) is the volume fraction of material 1 within the voxel at location x. Other voxels within the object may contain materials other than materials 1 and 2, but each voxel is modeled to have exactly two distinct materials. A CT image is provided by finding the volume fraction v for each voxel.

In the present invention it is necessary to impose the following requirements on the attenuation coefficients $\mu_1$ and $\mu_2$:
1) Both $\mu_1$ and $\mu_2$ must be monotonically decreasing with increasing E, and
2) The quantity $\mu_1 - \mu_2$ must be either positive and monotonically decreasing, or negative and monotonically increasing.

Although not always specifically noted in the present description, it is understood that the attenuation coefficients $\mu$ are functions of location x and photon energy E, and the volume fraction v is a function of location x.

Figure 3A:
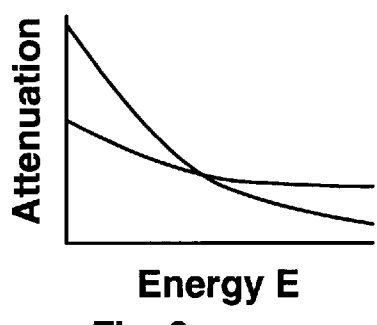
FIGS. 3a–3c illustrate an essential restriction on characteristics of attenuation spectra used in the present method.
Figure 3B:
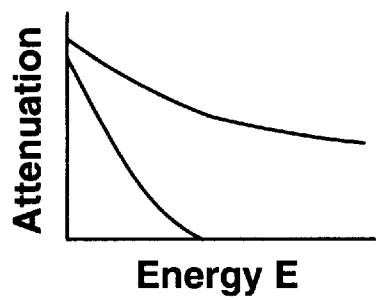
Figure 3C:
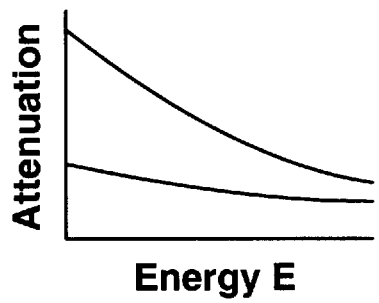

FIGS. 3a–3c illustrate requirement (2). FIG. 3a shows attenuation coefficients which cross, and therefore violate requirement (2). FIG. 3b shows attenuation coefficients for which $\mu_1 - \mu_2$ is either positive monotonic increasing or negative monotonic decreasing and therefore violate requirement (2). FIG. 3c shows an exemplary plot of attenuation coefficients that satisfy requirement (2).

Next we define an operator P that is linear in $\mu$:

$$P\mu(r) = \int \int S(E)\mu(x,E)dEdx.$$

It is noted that $P^{-1}$ exists and that $P^{-1}P \neq I$. This is true because $$\int S(E)\mu(x,E)dE = P^{-1}P\mu.$$

According to the single energy reconstruction method of the present invention, the volume fraction v(x) in the voxels comprising the object is found using the following algorithm:
1) Assume an initial estimate for v(x), given by $v^0(x)$.
2) Calculate a total estimated attenuation coefficient $\mu^k$ using the equation and the current estimate of v(x), given by $v^k(x)$ ($v^0(x) = v^k(x)$ in the first iteration):

$$\mu^k = v^k(x)\mu_1(x,E) + (1-v^k(x))\mu_2(x,E)$$

3) Calculate $\mu^{k+1}$ using the equation:

$$\mu^{k+1} = P^{-1}\{P\mu^k - B\mu^k + C(r)\}$$

where C(r) is the measured data.

4) Solve for $v^{k+1}$ in the following equation:

$$\mu^{k+1} = v^{k+1}\hat{\mu}_1 + (1-v^{k+1})\hat{\mu}_2$$

where:

$$\hat{\mu}_1 = \int S(E)\mu_1(x,E)dE, \text{ and}$$

$$\hat{\mu}_2 = \int S(E)\mu_2(x,E)dE.$$

5) Substitute $v^{k+1}$ for $v^k$ in step (2), and reiterate the process until successive values $v^{k+2}, v^{k+3}, v^{k+4}\ldots$ converge. In one particular embodiment, convergence is defined by:

$$\frac{\|B\mu^{k+1} - C(r)\|_2}{\|B\mu^k - C(r)\|_2} \geq 0.98.$$

Generally, the algorithm should be iterated at least twice for significant improvement over conventional techniques. More preferably, the algorithm is repeated 4–5 times. Significant improvements are generally not provided by repeating the algorithm more than 5 times.

The initial estimate $v^0$ does not need to be close to the final value of $v^0$ in order to arrive at a correct solution using the present method. However, an initial estimate close to the final value of the convergent series will reduce the number of iterations and the processing time.

It is noted that the present invention cannot be applied to a single voxel in isolation, unless the object comprises a single voxel. This is because calculations for every voxel affect calculations for other voxels, and the entire solution must be self-consistent.

DUAL ENERGY RECONSTRUCTION

In the dual energy reconstruction, it is assumed that the attenuation coefficient $\mu(x,E)$ can be expressed as a linear combination of two basis attenuation functions $\mu_1(x,E)$ and $\mu_2(x,E)$:

$$\mu(x,E) = A(x)\mu_1(x,E) + D(x)\mu_2(x,E),$$

where basis coefficients $A(x)$ and $D(x)$ are real numbers. The basis functions $\mu_1(x,E)$ and $\mu_2(x,E)$ do not necessarily correspond to attenuation coefficients of any known material. In a particular object comprising many voxels, each voxel may be modeled by different basis attenuation functions. For example, a single object may comprise several basis attenuation functions, but any particular voxel is associated with exactly two basis attenuation functions.

Just as in the single energy method, it is necessary to impose the following requirements on the basis attenuation functions and $\mu_2$:

1) Both $\mu_1$ and $\mu_2$ must be monotonically decreasing with increasing E, and
2) The quantity $\mu_1 - \mu_2$ must be either positive and monotonically decreasing, or negative and monotonically increasing.

In the dual energy reconstruction, two scans of the object must be performed with distinct X-ray beam spectra, $S_1(E)$ and $S_2(E)$. The beam spectra $S_1(E)$ and $S_2(E)$ can be provided by applying different accelerating voltages to an X-ray tube (e.g. 80 kV and 120 kV as known in the art), or by placing different X-ray filters in the X-ray beam. Many different techniques for altering the X-ray spectrum are well known in the art and are often used in X-ray tomography.

In the dual energy reconstruction, the attenuation spectrum for a voxel is characterized when coefficients $A(x)$ and $D(x)$ are found. The attenuation spectrum may be used to identify materials within the voxel, or for other purposes.

According to the dual energy reconstruction method of the present invention, the basis coefficients A and D are found by using the following algorithm:

1) Assume initial estimates for basis coefficients $A(x)$ and $D(x)$, given by $A^0(x)$ and $D^0(x)$.
2) Calculate $\mu^k$ using the equation and the current estimates of A and D, given by $A^k(x)$ and $D^k(x)$ ($A^0(x) = A^k(x)$ and $D^0(x) = D^k(x)$ in the first iteration):

$$\mu^k(x,E) = A^k(x)\mu_1(x,E) + D^k(x)\mu_2(x,E)$$

3) Using $\mu^k$, calculate $\mu^{k+1,S1}$ for the spectrum $S_1(E)$ using the equation:

$$\mu^{k+1,S1} = P^{-1}\{P\mu^k - B\mu^k + C(r)\},$$

where operators P, B, and C(r) are defined with respect to $S_1(E)$.

4) Using $\mu^k$, calculate $\mu^{k+1,S2}$ for the spectrum $S_2(E)$ using the equation:

$$\mu^{k+1,S2} = P^{-1}\{P\mu^k - B\mu^k + C(r)\},$$

where operators P, B, and C(r) are defined with respect to $S_2(E)$.

5) Calculate $A^{k+1}$ and $D^{k+1}$ using the following simultaneous equations:

$$\mu^{k+1,S1} = A^{k+1}\hat{\mu}_{1,S1} + D^{k+1}\hat{\mu}_{2,S1}, \text{ and}$$

$$\mu^{k+1,S2} = A^{k+1}\hat{\mu}_{1,S2} + D^{k+1}\hat{\mu}_{2,S2},$$

where $\hat{\mu}_{1,S1} = \int S_1(E)\mu_1(E)dE$, $\hat{\mu}_{1,S2} = \int S_2(E)\mu_1(E)dE$, $\hat{\mu}_{2,S1} = \int S_1(E)\mu_2(E)dE$, and $\hat{\mu}_{2,S2} = \int S_2(E)\mu_2(E)dE$.

6) Substitute $A^{k+1}$ and $D^{k+1}$ in step (2), and reiterate the process until successive values $A^{k+1}, A^{k+2}\ldots$ and $D^{k+1}, D^{k+2}\ldots$ converge. In one particular embodiment, convergence is defined by:

$$\frac{\|B\mu^{k+1} - C(r)\|_2}{\|B\mu^k - C(r)\|_2} \geq 0.98 \text{ for } S_1(E) \text{ and } S_2(E)$$

After being computed, the coefficients A and D and basis attenuation functions $\mu_1$ and $\mu_2$ can be used to reconstruct the attenuation spectra of individual voxels. The reconstructed attenuation spectrum can be used to identify materials in the object, or for many other purposes such as bone density measurements.

As in the single energy method, the dual energy method cannot be applied to a single voxel in isolation, unless the object comprises a single voxel. This is because calculations for every voxel affects calculations for other voxels, and the entire solution must be self-consistent.

The methods of the present invention provide improvements in beam hardening errors. Further applications of the present invention to signal processing from X-ray tomography will be apparent to one skilled in the art.

PROOF

This section contains the theoretical foundation for the iterative Single energy reconstruction algorithm. We show that the reconstruction problem can be formulated as a fixed point problem and the Banach fixed point theorem ensures that the algorithm will always converge to a unique solution. For ease of understanding, we divide the proof into two theorems. Theorem 1 uses the results from Theorem 2 to illustrate the unique convergence properties of the iterative algorithm.

Theorem 1 (Iterative polychromatic reconstruction)

Let m*(x,E) be an unknown attenuation function which can be expressed by a two mixture model:

$$\mu^*(x,E) = v^*(x)\mu_1(x,E) + (1-v^*(x))\mu_2(x,E)$$

where v*(x) is the volume fraction of the first material at location x and $\mu_1$, $\mu_2$ are attenuation spectra of the two known materials, with the following properties:
1) For any x, $\mu_1$ and $\mu_2$ are monotonically decreasing functions with respect to E.
2) For any x, the quantity $\mu_1-\mu_2$ is a positive monotonically decreasing function with respect to E.

Let C=Bμ* be the polychromatic projection of m* with respect to the polychromatic spectrum S(E). Then the sequence $\{v^k\}$ which satisfies:

$$v^k\hat{\mu}_1 + (1-v^k)\hat{\mu}_2 = P^{-1}\{P\mu^{k-1} - B\mu^{k-1} + C\}$$

where $$\mu^{k-1} = v^{k-1}\mu_1 + (1-v^{k-1})\mu_2,$$

$$\hat{\mu}_1 = \int S(E)\mu_1(x,E)dE,$$

and $$\hat{\mu}_2 = \int S(E)\mu_2(x,E)dE,$$

converges to the true volume fraction function v* independent of the initial estimate $v^0$.

In the above problem, the true volume fraction v* is a fixed point mapping T, $$V^* = T(v^*),$$

where T is defined as $$w = T(v): w\hat{\mu}_1 + (1-w)\hat{\mu}_2 = P^{-1}\{P(v\mu_1 + (1-v)\mu_2) - B(v\mu_1 + (1-v)\mu_2) + C\}$$

The Banach fixed point theorem states that if T is a contraction on the space of volume fraction V, $$\forall x, y \in V, \exists \alpha \in \mathfrak{R}, \alpha \leq 1 \text{ such that } \|T(x) - T(y)\| \leq \alpha \|x - y\|,$$

then T has precisely one fixed point and the iterative sequence $\{v^k\}$, from the procedure $v^k = T(v^{k-1})$ converges to the unique fixed point v* of T with arbitrary $v^0 \in V$. Hence, proving that T is a contraction on V is sufficient.

Let $v_a$, $v_b$ be any two volume fraction functions and $\mu_a, \mu_b, p_a, p_b, w_a, w_b$ be defined as follows:

$$\mu_a = v_a\mu_1 + (1-v_a)\mu_2$$

$$\mu_b = v_b\mu_1 + (1-v_b)\mu_2$$

$$p_a = P\mu_a - B\mu_a + C$$

$$p_b = P\mu_b - B\mu_b + C$$

$$w_a = T(v_a)$$

$$w_b = T(v_b)$$

Defining $f(r,E) = \int_r \mu_a(x,E)dx$ and $g(r,E) = \int_r \mu_b(x,E)dx$, we have $$|P_a(r) - P_b(r)| = |E\{f\} - E\{g\} - [\log E\{\exp(-f)\}] + [\log E\{\exp(-g)\}]|$$

where the expectation is taken with respect to the beam spectrum profile S(E). Using the results from the above equation leads to $$|P_a(r) - P_b(r)| \leq |E\{f\} - E\{g\}| = |P\mu_a - P\mu_b|.$$

Taking $p^{-1}$ on both sides of the above equation leads to $$|\int_r (w_a(x) - w_b(x))(\hat{\mu}_1(x) - \hat{\mu}_2(x))dx| \leq |\int_r (v_a(x) - v_b(x))(\hat{\mu}_1(x) - \hat{\mu}_2(x))dx|$$

The above inequality is equivalent to $$\|w_a - w_b\| \leq \|v_a - v_b\|$$

$$\|T(v_a) - T(v_b)\| \leq \|v_a - v_b\|$$

where the norm is defined as $$v \in V, \|v\| = \int |\int_r v(r)(\hat{\mu}_1(x) - \hat{\mu}_2(x))dx|dr$$

Thus T is a contraction on V.

Theorem 2

Let f and g be positive monotonically decreasing functions such that f—g is a positive monotonically decreasing function, then $$E\{f\} - E\{g\} > [-\log E\{\exp(-f)\}] - [-\log E\{\exp(-g)\}]$$

where the expectation is taken with respect to any probability density function.

Proof

Let the expectation be based on probability density function h. We define $t:[0,1] \to \mathfrak{R}$ as $$t(\alpha) = E_h\{g + \alpha(f-g)\} - [-\log E_h\{\exp(-g - \alpha(f-g))\}]$$

By Jensens inequality, $t(0) \geq 0$. Differentiating with respect to α, we have $$\frac{dt}{d\alpha} = E_h\{f-g\} - \frac{E_h\{(f-g)\exp(-g-\alpha(f-g))\}}{E_h\{\exp(-g-\alpha(f-g))\}}$$

$$\frac{dt}{d\alpha} = E_h\{f-g\} - E_{h'}\{f-g\}$$

where h' is a probability density function defined by $$h' = \frac{\exp(-g - \alpha(f-g))}{E_h\{\exp(-g-\alpha(f-g))\}} h$$

Since f and g are monotonically decreasing functions, exp(—g—α(f—g—)) is a monotonically increasing function for any $\alpha \in [0,1]$.

Thus we conclude that $$\frac{dt}{d\alpha} = E_h\{f-g\} - E_{h'}\{f-g\} > 0 \text{ for any } \alpha \in [0, 1]$$

This shows that t is a monotonically increasing function. Thus we have t(1)>t(0), which is equivalent to:

$$E\{f\} - E\{g\} > [-\log E\{\exp(-f)\}] - [-\log E\{\exp(-g)\}].$$

It will be clear to one skilled in the art that the above embodiment may be altered in many ways without departing from the scope of the invention. Accordingly, the scope of the invention should be determined by the following claims and their legal equivalents.

What is claimed is:

1. A method for calculating characteristics of an object comprising voxels using an X-ray computer assisted tomography device, comprising the steps of:
   a) projecting through the object an X-ray beam having a known energy spectrum indicated by S(E);

b) detecting the X-rays with an X-ray detector;
c) repeating steps (a) and (b) for at least two different orientations of the X-ray beam with respect to the object;
d) defining a first material and a second material within each voxel, wherein the first and second materials have known distinct attenuation spectra, given by $\mu_1(x,E)$ and $\mu_2(x,E)$, respectively, such that a total attenuation coefficient $\mu(x,E)$ of the object is given by:

$$\mu(x,E)=v(x)\mu_1(x,E)+(1-v(x))\mu_2(x,E)$$

where $v(x)$ is a number between 0 and 1 and indicates a volume fraction of each voxel comprised of the first material;
e) defining an initial estimated volume fraction $v^k(x)$;
f) calculating an estimated total attenuation coefficient $\mu^k(x,E)$ from the equation;

$$\mu^k(x,E)=v^k(x)\mu_1(x,E)+(1-v^k(x))\mu_2(x,E)$$

g) calculating a new estimated total attenuation coefficient $\mu^{k+1}(x,E)$ from the following equation:

$$\mu^{k+1}(x,E)=P^{-1}\{P\mu^k(x,E)-B\mu^k(x,E)+C(r)\}$$

where P is an operator defined by $P\mu=\int_r \int S(E)\mu(E)dEdx$, B is an operator defined by $B\mu=-\log\int S(E)\exp(\int_r \mu(E)dx)dE$, and $C(r)$ represents X-ray detector output, and r indicates the X-ray beam path;
h) calculating a new estimated volume fraction $v^{k+1}$ from the following equation:

$$\mu^{k+1}(x,E)=v^{k+1}(x,E)\hat{\mu}_1(x,E)+(1-v^{k+1}(x))\hat{\mu}_2(x,E)$$

where $\hat{\mu}_1(E)=\int S(E)\mu_1(E)dE$ and $\hat{\mu}_2(E)=\int S(E)\mu_2(E)dE$
i) repeating steps (f), (g) and (h) using the new estimated volume fraction $v^{k+1}(x)$ instead of the initial estimated volume fraction $v^k(x)$.

2. The method of claim 1 wherein steps (f), (g), and (h) are repeated using a successive value of the estimated volume fraction $v^{k+2}$.

3. The method of claim 1 wherein steps (f), (g), and (h) are repeated 4 times using successive values of the estimated volume fraction.

4. The method of claim 1 wherein steps (f), (g), and (h) are repeated until $$\frac{\|B\mu^{k+1}-C(r)\|_2}{\|B\mu^k-C(r)\|_2} \geq 0.98.$$

5. A method for calculating characteristics of an object comprising voxels using an X-ray computer assisted tomography device, comprising the steps of:
a) projecting through the object a first X-ray beam having a known energy spectrum indicated by $S_1(E)$;
b) detecting the first X-ray beam with an X-ray detector;
c) repeating steps (a) and (b) for at least two different orientations of the first X-ray beam with respect to the object;
d) projecting through the object a second X-ray beam having a known energy spectrum indicated by $S_2(E)$;
e) detecting the second X-ray beam with an X-ray detector;
f) repeating steps (d) and (e) for at least two different orientations of the second X-ray beam with respect to the object;
g) defining a first basis attenuation function and a second basis attenuation function, given by $\mu_1(x,E)$ and $\mu_2(x,E)$, respectively, such that a total attenuation coefficient $\mu(x,E)$ of the voxel is given by:

$$\mu(x,E)=A(x)\mu_1(x,E)+D(x)\mu_2(x,E)$$

where coefficients A and D are real numbers;
h) defining initial coefficients $A^k$ and $D^k$;
i) calculating an estimated total attenuation coefficient $\mu^k(x,E)$ from the equation;

$$\mu^k(x)(x,E)=A^k(x)\mu_1(x,E)+D^k(x)\mu_2(x,E)$$

j) calculating a new estimated total attenuation coefficient $\mu^{k+1,S1}(x,E)$ associated with spectrum $S_1(E)$ from the following equation:

$$\mu^{k+1,S1}(x,E)=P_{S1}^{-1}\{P_{S1}\mu^k(x,E)-B_{S1}\mu^k(x,E)+C_1(r)\}$$

where $P_{S1}$ is an operator defined by $P_{S1}\mu=\int_r \int S_1(E)\mu(E)dEdx$, $B_{S1}$ is an operator defined by $B_{S1}\mu=-\log\int S_1(E)\exp(\int_r(E)dx)dE$, and $C_1(r)$ represents X-ray detector output associated with $S_1(E)$;
k) calculating a new estimated total attenuation coefficient $\mu^{k+,S2}(x,E)$ from the following equation:

$$\mu^{k+1,S2}(x,E)=P_{S2}^{-1}\{P_{S2}\mu^k(x,E)-B_{S2}\mu^k(x,E)+C_{S2}(r)\}$$

where $P_{S2}$ is an operator defined by $P_{S2}\mu=\int_r \int S_2(E)\mu(E)dEdx$, $B_{S2}$ is an operator defined by $B_{S2}\mu=-\log \int S_2(E)\exp(\int_r\mu(E)dx)dE$, and $C_2(r)$ represents X-ray detector output associated with $S_2(E)$;
l) calculate new estimated coefficients $A^{k+1}(x)$ and $D^{k+1}(x)$ from the following simultaneous equations:

$$\mu^{k+1,S1}(x,E)=A^{k+1}(x)\hat{\mu}_{1,S1}(x,E)+D^{k+1}(x)\hat{\mu}_{2,S1}(x,E), \text{ and}$$

$$\mu^{k+1,S2}(x,E)=A^{k+1}(x)\hat{\mu}_{1,S2}(x,E)+D^{k+1}(x)\hat{\mu}_{2,S2}(x,E),$$

where $$\hat{\mu}_{1,S1}(x)=\int S_1(E)\mu_1(x,E)dE, \hat{\mu}_{1,S2}(x)=\int S_2(E)\mu_1(x,E)dE,$$

$$\hat{\mu}_{2,S1}(x)=\int S_1(E)\mu_2(x,E)dE, \text{ and } \hat{\mu}_{2,S2}(x)=\int S_2(E)\mu_2(x,E)dE;$$

m) repeating steps (i), (j), (k) and (l) using the new estimated coefficients $A^{k+1}(x)$ and $D^{k+1}(x)$ instead of the initial estimated coefficients $A^k(x)$ and $D^k(x)$.

6. The method of claim 5 wherein steps (i), (j), (k) and (l) are repeated using successive values of the estimated coefficients $A^{k+2}(x)$ and $D^{k+2}(x)$.

7. The method of claim 5 wherein steps (i), (j), (k) and (l) are repeated 4 times using successive values of the estimated coefficients.

8. The method of claim 5 wherein steps (i), (j), (k) and (l) are repeated until $$\frac{\|B_{S1}\mu^{N+1}-C_1(r)\|_2}{\|B_{S1}\mu^N-C_1(r)\|_2} \geq 0.98 \text{ and}$$

$$\frac{\|B_{S2}\mu^{N+1}-C_2(r)\|_2}{\|B_{S2}\mu^N-C_2(r)\|_2} \geq 0.98,$$

where N is an integer indicating number of algorithm iterations.

* * * * *